United States Patent
Bambal et al.

(10) Patent No.: US 10,577,293 B2
(45) Date of Patent: Mar. 3, 2020

(54) PROCESS AND APPARATUS FOR IMPROVED PARA-XYLENE YIELD IN AN AROMATIC COMPLEX

(71) Applicant: UOP LLC, Des Plaines, IL (US)

(72) Inventors: Ashish Suresh Bambal, Arlington Heights, IL (US); Anton N. Mlinar, Vernon Hills, IL (US); James A. Johnson, Burr Ridge, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/491,796

(22) Filed: Apr. 19, 2017

(65) Prior Publication Data

US 2018/0305277 A1   Oct. 25, 2018

(51) Int. Cl.
*C07C 5/27* (2006.01)
*C07C 5/22* (2006.01)

(52) U.S. Cl.
CPC ............ *C07C 5/2732* (2013.01); *C07C 5/277* (2013.01)

(58) Field of Classification Search
CPC ........... C07C 2/66; C07C 5/27; C07C 5/2705; C07C 5/2702
See application file for complete search history.

(56) References Cited

U.S. PATENT DOCUMENTS

| | | | |
|---|---|---|---|
| 6,004,452 A * | 12/1999 | Ash et al. | C10G 51/06 208/80 |
| 6,376,736 B1 * | 4/2002 | Rutten et al. | C07C 7/00 585/815 |
| 6,448,459 B1 | 9/2002 | Magne-Drisch | |
| 6,740,788 B1 | 5/2004 | Maher et al. | |
| 7,812,208 B2 | 10/2010 | Cheng et al. | |
| 7,820,869 B2 | 10/2010 | Priegnitz et al. | |
| 7,915,471 B2 | 3/2011 | Leflaive et al. | |
| 8,283,274 B2 | 10/2012 | Cheng et al. | |
| 9,469,579 B2 | 10/2016 | Molinier et al. | |
| 2008/0262282 A1 * | 10/2008 | Leflaive et al. | C07C 15/08 585/745 |

(Continued)

FOREIGN PATENT DOCUMENTS

FR   3023840 A1   1/2016

OTHER PUBLICATIONS

Exxonmobil, The leading edge in xylenes isomerization.

(Continued)

*Primary Examiner* — Youngsul Jeong (57) ABSTRACT

Processes and apparatuses for producing para-xylenes are provided. The processes comprises providing a hydrocarbon stream comprising C7+ hydrocarbons. The hydrocarbon stream is separated to provide a C8 aromatics stream and an ortho-xylene rich stream. The C8 aromatics stream is passed to a para-xylene separation unit for separating para-xylene to provide a para-xylene stream and a raffinate stream. At least a portion of the raffinate stream is passed to a first isomerization unit to provide a first isomerization effluent, wherein the first isomerization effluent is produced in the presence of an ethylbenzene (EB) isomerization catalyst. At least a portion of the ortho-xylene rich stream is contacted with an isomerization catalyst in a second isomerization unit in liquid phase at isomerization conditions in substantial absence of hydrogen to produce a second isomerization effluent.

20 Claims, 2 Drawing Sheets

(56) References Cited

U.S. PATENT DOCUMENTS

2009/0326308 A1   12/2009   Kulprathipanja et al.
2012/0108868 A1    5/2012   Pilliod et al.
2015/0065768 A1    3/2015   Bresler et al.

OTHER PUBLICATIONS

International Search Report from corresponding PCT application No. PCT/US2018/027906, dated Aug. 2, 2018.
Written Opinion from corresponding PCT application No. PCT/US2018/027906, dated Jul. 17, 2018.

* cited by examiner

PROCESS AND APPARATUS FOR IMPROVED PARA-XYLENE YIELD IN AN AROMATIC COMPLEX

TECHNICAL FIELD

The technical field generally relates to apparatuses and processes for producing xylene isomers in an aromatics complex. More particularly, the present disclosure relates to integration of a liquid phase isomerization unit in an aromatics complex to improve the para-xylene yield.

BACKGROUND

Most new aromatics complexes are designed to maximize the yield of benzene and $C_8$ aromatic isomer (para-xylene, meta-xylene, ethylbenzene and ortho-xylene). Para-xylene, meta-xylene and ortho-xylene, are important intermediates which find wide and varied application in chemical syntheses. Para-xylene upon oxidation yields terephthalic acid which is used in the manufacture of synthetic textile fibers and resins. Meta-xylene is used in the manufacture of thermoplastic resins, plasticizers, azo dyes, wood preservers, etc. Ortho-xylene is feedstock for phthalic anhydride production. The distribution of xylene isomers from catalytic reforming and other sources generally does not match that of the sought isomers for chemical intermediates and thus the producer converts the feedstocks to generate more of the sought isomers in the aromatics complexes.

The production of xylenes is practiced commercially in large-scale facilities and is highly competitive. Concerns exist not only about the efficient conversion of feedstock through one or more of isomerization, transalkylation and disproportionation steps to produce xylenes, but also other competitive aspects with respect to such facilities including capital costs and energy costs.

A prior art aromatics complex flow scheme has been disclosed by Meyers in the HANDBOOK OF PETROLEUM REFINING PROCESSES, 2d. Edition in 1997 by McGraw-Hill.

In an aromatics complex, the para-xylene lean stream from para-xylene separation unit is typically routed to the isomerization unit to re-establish the xylene equilibrium and convert ethyl benzene (EB). In vapor phase, the isomerization process with EB dealkylation type catalyst, ethyl benzene is dealkylated to form benzene and xylenes are isomerized to establish equilibrium. On the other hand, the isomerization process with EB isomerization type catalyst converts ethyl benzene in the feed to xylenes via a naphthene intermediate pathway while still reestablishing xylene equilibrium. The performance of the EB isomerization unit is highly sensitive to the ortho-xylene content of the feed with higher ortho-xylene levels leading to higher operating temperatures and therefore higher ring losses. Much of this additional ring loss is from ring opening and cracking (unrecoverable) leading to lower xylene yields in the aromatics complex.

Accordingly, it is desirable to provide an improved process and apparatus for production of para-xylene that can lower the yield losses occurring in the EB isomerization unit to improve para-xylene production. Further, it is desirable to control the amount of ortho-xylene being fed to the EB isomerization unit. Furthermore, other desirable features and characteristics of the present subject matter will become apparent from the subsequent detailed description of the subject matter and the appended claims, taken in conjunction with the accompanying drawings and this background of the subject matter.

BRIEF SUMMARY

Various embodiments contemplated herein relate to apparatuses and processes for producing para-xylene in an aromatics complex. The exemplary embodiments taught herein illustrate integration of the liquid phase isomerization unit in an aromatics complex producing para-xylenes.

In accordance with an exemplary embodiment, a process is provided for the production of para-xylene comprising providing a hydrocarbon stream comprising $C_{7+}$ hydrocarbons. The hydrocarbon stream is separated to provide a $C_8$ aromatics stream and an ortho-xylene rich stream. The $C_8$ aromatics stream is passed to a para-xylene separation unit for separating para-xylene to provide a para-xylene stream and a raffinate stream. At least a portion of the raffinate stream is passed to a first isomerization unit to provide a first isomerization effluent, wherein the first isomerization effluent is produced in the presence of an ethylbenzene (EB) isomerization catalyst. At least a portion of the ortho-xylene rich stream is contacted with an isomerization catalyst in a second isomerization unit in liquid phase at isomerization conditions in substantial absence of hydrogen to produce a second isomerization effluent.

In accordance with another exemplary embodiment, a process is provided for the production of para-xylene comprising providing a reformate stream comprising aromatic hydrocarbons to a reformate splitter to provide a reformate bottoms stream comprising $C_{7+}$ aromatic hydrocarbons and a reformate overhead stream comprising $C_{7-}$ aromatic hydrocarbons. The reformate bottoms stream is passed to a xylene column to provide an $C_8$ aromatics stream and a xylene bottoms stream comprising ortho-xylenes and $C_{9+}$ alkylaromatic hydrocarbons. The $C_8$ aromatics stream is passed to a para-xylene separation unit for separating para-xylene, wherein the $C_8$ aromatics stream is contacted with an adsorbent under adsorption conditions to provide a para-xylene stream and a raffinate stream. The xylene bottoms stream is passed to an ortho-xylene column to provide the ortho-xylene rich stream and an ortho-xylene column bottoms stream comprising $C_{9+}$ alkylaromatic hydrocarbons. At least a portion of the raffinate product stream is passed to a first isomerization unit to provide a first isomerization effluent, wherein the first isomerization effluent is produced in the presence of an ethylbenzene (EB) isomerization catalyst. At least a portion of the ortho-xylene rich stream is contacted with an isomerization catalyst in a second isomerization unit in liquid phase at isomerization conditions in substantial absence of hydrogen to produce a second isomerization effluent.

In accordance with yet another exemplary embodiment, a process is provided for the production of para-xylene comprising providing a reformate stream comprising aromatic hydrocarbons to a reformate splitter to provide a reformate bottoms stream comprising $C_{7+}$ aromatic hydrocarbons and a reformate overhead stream comprising $C_{7-}$ aromatic hydrocarbons. The reformate bottoms stream is passed to a xylene column to provide a $C_8$ aromatics stream from an overhead, an ortho-xylene rich stream as a side draw and a xylene column bottoms stream comprising $C_{9+}$ alkylaromatic hydrocarbons. The $C_8$ aromatics stream is passed to a para-xylene separation unit for separating para-xylene to provide a para-xylene stream and a raffinate stream. At least a portion of the raffinate stream is passed to a first isomerization unit to provide a first isomerization effluent, wherein the first isomerization effluent is produced in the presence of an ethylbenzene (EB) isomerization catalyst. At least a portion of the ortho-xylene rich stream contacted with an isomerization catalyst in a second isomerization unit in liquid phase at isomerization conditions in substantial absence of hydrogen to produce a second isomerization effluent.

These and other features, aspects, and advantages of the present disclosure will become better understood upon consideration of the following detailed description, drawings and appended claims.

BRIEF DESCRIPTION OF THE DRAWINGS

The various embodiments will hereinafter be described in conjunction with the following FIGURES, wherein like numerals denote like elements.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

Definitions

As used herein, the term "stream" can include various hydrocarbon molecules and other substances.

As used herein, the term "stream", "feed", "product", "part" or "portion" can include various hydrocarbon molecules, such as straight-chain and branched alkanes, naphthenes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

As used herein, the term "overhead stream" can mean a stream withdrawn at or near a top of a vessel, such as a column.

As used herein, the term "bottoms stream" can mean a stream withdrawn at or near a bottom of a vessel, such as a column.

Hydrocarbon molecules may be abbreviated $C_1$, $C_2$, $C_3$, Cn where "n" represents the number of carbon atoms in the one or more hydrocarbon molecules or the abbreviation may be used as an adjective for, e.g., non-aromatics or compounds. Similarly, aromatic compounds may be abbreviated $A_6$, $A_7$, $A_8$, An where "n" represents the number of carbon atoms in the one or more aromatic molecules. Furthermore, a superscript "+" or "−" may be used with an abbreviated one or more hydrocarbons notation, e.g., $C_{3+}$ or $C_{3-}$, which is inclusive of the abbreviated one or more hydrocarbons. As an example, the abbreviation "$C_{3+}$" means one or more hydrocarbon molecules of three or more carbon atoms.

As used herein, the term "unit" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top or overhead pressure is the pressure of the overhead vapor at the vapor outlet of the column. The bottom temperature is the liquid bottom outlet temperature. Overhead lines and bottoms lines refer to the net lines from the column downstream of any reflux or reboil to the column unless otherwise shown. Stripping columns omit a reboiler at a bottom of the column and instead provide heating requirements and separation impetus from a fluidized inert media such as steam.

As used herein, the term "rich" can mean an amount of at least generally 30%, preferably 70% and more preferably 90%, by mole, of a compound or class of compounds in a stream.

As depicted, process flow lines in the FIGURES can be referred to interchangeably as, e.g., lines, pipes, feeds, gases, products, discharges, parts, portions, or streams.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "direct communication" means that flow from the upstream component enters the downstream component without undergoing a compositional change due to physical fractionation or chemical conversion.

The term "predominantly" means a majority, suitably at least 50 mol % and preferably at least 60 mol %.

The term "passing" means that the material passes from a conduit or vessel to an object.

As used herein, the term "substantial" can mean an amount of at least generally about 80%, preferably about 90%, and optimally about 99%, by weight, of a compound or class of compounds in a stream.

The terms "application" and "program" refer to one or more computer programs, software components, sets of instructions, procedures, functions, objects, classes, instances, related data, or a portion thereof adapted for implementation in a suitable computer code (including source code, object code, or executable code). The term "communicate," as well as derivatives thereof, encompasses both direct and indirect communication.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description. Moreover, the reaction conditions including selection of temperature, pressure, LHSV and catalyst in the various units in the aromatics complex described below are conventional which are known to one of ordinary skill in the art, unless wherever mentioned.

Figure 1:
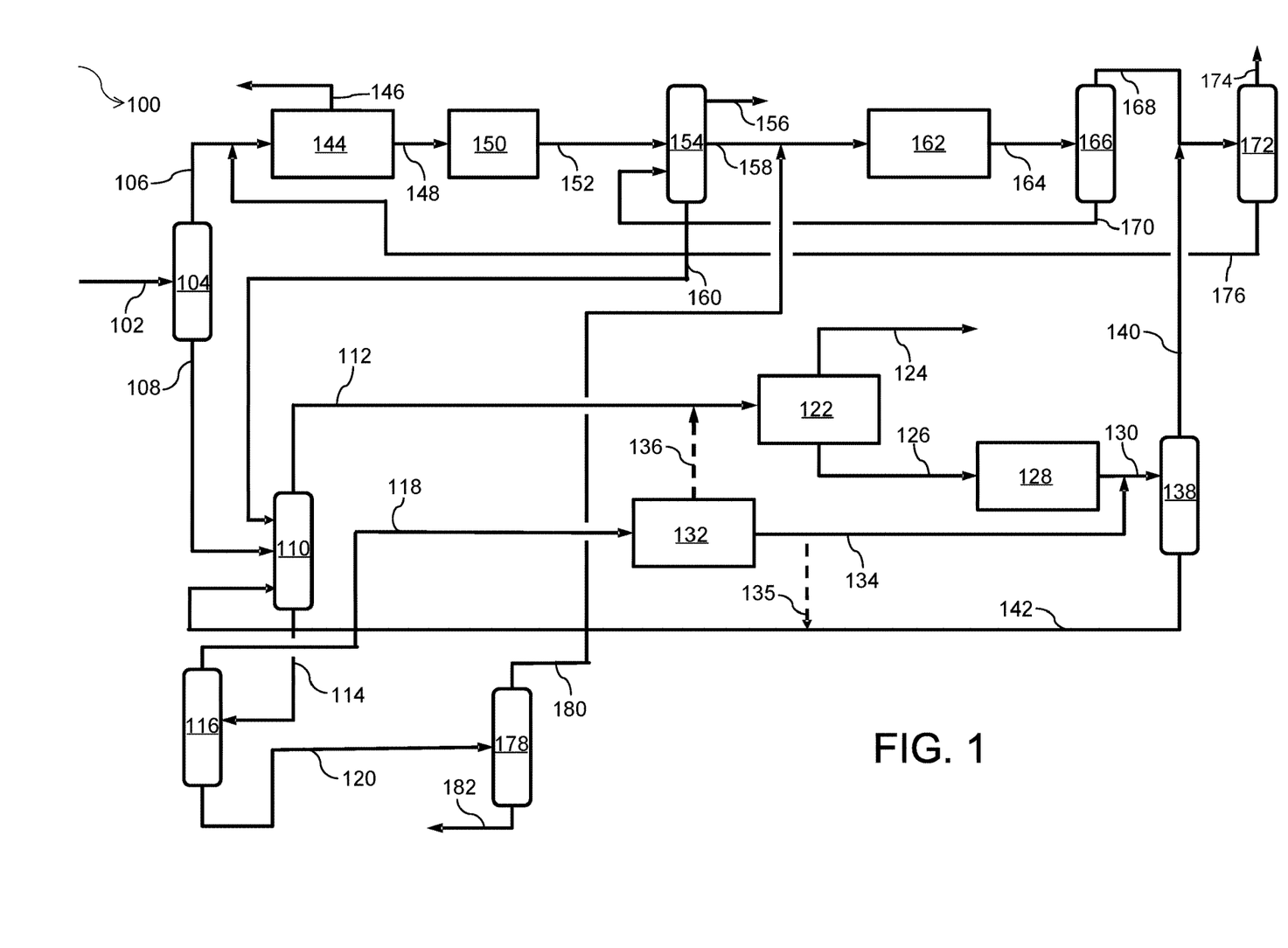
FIG. 1 illustrates an aromatics complex according to an embodiment of the present disclosure.

Various embodiments are directed to apparatuses and processes for producing a $C_8$ aromatic isomer product in an aromatic complex. An exemplary embodiment of the process and apparatus for producing a para-xylene product in an aromatic complex is addressed with reference to a process and apparatus 100 illustrating an aromatics complex according to an embodiment as shown in FIG. 1. The process and apparatus 100 includes a reformate splitter column 104, a xylene column 110, an ortho-xylene column 116, a para-xylene separation unit 122, a first isomerization unit 128, a second isomerization unit 132, a deheptanizer column 138, an aromatics extraction unit 144, a clay treater 150, a benzene-toluene (BT) column 154, a transalkylation unit 162, a transalkylation stripper 166, a stabilizer 172 and a heavy aromatics column 178.

In various embodiments, a hydrocarbon stream comprising $C_{7+}$ hydrocarbons is provided and separated to provide a $C_8$ aromatics stream and an ortho-xylene rich stream. In accordance with an exemplary embodiment as shown in FIG. 1, a reformate stream in line 102 comprising aromatic hydrocarbons may be passed to the reformate splitter column 104. A reformate overhead stream in line 106 comprising $C_{7-}$ aromatic hydrocarbons and a reformate bottoms stream in line 108 comprising $C_{7+}$ aromatic hydrocarbons may be withdrawn from the reformate splitter column 104. In accordance with an exemplary embodiment as shown, an overhead stream from the reformate splitter column 106 may be condensed and separated in a receiver with a portion of the condensed liquid being refluxed back to the reformate splitter column 104 to obtain the reformate overhead stream from a net portion in line 106. Further, in an exemplary embodiment, the reformate splitter column 104 may include a reboiler at a bottom of the column to vaporize and send a portion of the reformate bottoms stream back to the bottom of the column.

The reformate bottoms stream may be passed to a xylene column to provide the $C_8$ aromatics stream from an overhead and a xylene bottoms stream comprising ortho-xylenes and $C_{9+}$ alkylaromatic hydrocarbons. In accordance with an exemplary embodiment as shown in FIG. 1, the reformate bottoms stream in line 108 may be passed to the xylene column 110 for separation. The xylene column 110 may further receive a benzene-toluene (hereinafter "BT") column bottoms stream in line 160 comprising xylenes. Further, the xylene column 110 may receive $C_{8+}$ aromatic hydrocarbons in a deheptanizer bottoms stream in line 142 from the deheptanizer column 138. In an aspect, the reformate bottoms stream in line 108 may be passed through an olefin treatment unit to treat residual olefin contaminants before being passed to the xylene column 110. Examples of the olefin treatment unit include, but are not limited to, a clay treater and an olefin reduction process (ORP) unit may be passed through a clay treater prior to being passed to the xylene column 110.

The xylene column 110 separates concentrated $C_8$ aromatic comprising para-xylene, meta-xylene and ethyl benzene as a $C_8$ aromatics stream in line 112 from a xylene bottoms stream comprising ortho-xylenes and $C_{9+}$ alkylaromatic hydrocarbons in line 114. The $C_8$ aromatics stream in line 112 is withdrawn from an overhead and a xylene bottoms stream in line 114 comprising ortho-xylene is withdrawn from the bottoms of the xylene column 110. As shown in FIG. 1, the $C_8$ aromatics stream in line 112 may be passed to the para-xylene separation unit 122 for separating para-xylene to provide a para-xylene stream in line 124 and a raffinate stream in line 126. Further, the xylene bottoms stream in line 114 may be passed to the ortho-xylene column 116 for separation.

In accordance with an exemplary embodiment, an energy efficient aromatics complex may include a first xylene column and a second xylene column (not shown). In such an embodiment, reformate bottoms stream in line 108 and the BT column bottoms stream in line 160 may be provided to the first xylene column and the deheptanizer bottoms stream in line 142 may be passed to the second xylene column. Further, in the instant aspect, the bottoms of first xylene column may be passed to the ortho-xylene column 116 for separation of the ortho-xylene. In another aspect, the ortho-xylene column 116 may be in communication with the second xylene column and bottoms of the second xylene column may be passed to the ortho-xylene column 116 for separation.

In an alternative embodiment, the deheptanizer column and the first xylene column may be combined to provide an aromatics stripper column and the second xylene column may be the aromatics rerun column. In the instant flow scheme, the reformate bottoms stream in line 108 may be passed to the aromatics stripper column and bottoms of the aromatics stripper column may be passed to the ortho-xylene column for separation of ortho-xylene from the heavier hydrocarbons being passed to the aromatics rerun column to extract the remaining $C_8$ aromatics. In another aspect, the ortho-xylene column 116 may be in communication with the aromatics rerun column and bottoms of the aromatics rerun column may be passed to the ortho-xylene column 116.

Referring back to FIG. 1, the $C_8$ aromatics stream in line 112 comprising para-xylene, meta-xylene and ethyl benzene is withdrawn and may be passed to the para-xylene separation unit 122 for separating para-xylene to provide a para-xylene stream in line 124 and a raffinate stream in line 126.

In the para-xylene separation unit 122, the $C_8$ aromatics stream may be contacted with an adsorbent under adsorption conditions to provide the para-xylene stream in line 124 and the raffinate stream in line 126. In an embodiment, the adsorption conditions may include an adsorption temperature of less than about 175° C. (350° F.). In accordance with an exemplary embodiment, the adsorbent may be a binderless adsorbent comprising zeolite X having an average crystallite size of less than 1.8 microns. In an exemplary aspect, the adsorbent may have at least 95% of its ion-exchangeable sites exchanged with barium or a combination of barium and potassium. In accordance with an exemplary embodiment, the binderless adsorbent may include a converted portion of zeolite X resulting from the conversion of a zeolite X-precursor. Examples of the zeolite X-precursor include, but are not limited to, kaolin clay. Binderless adsorbents that can be used in the present disclosure include conventional binderless zeolite adsorbents such as those disclosed in U.S. Pat. Nos. 8,283,274, 7,812,208, 7,820,869, and U.S. Pat. Publ. No. 2009/0326308, the teachings of which are incorporated herein by reference.

In accordance with an exemplary embodiment, the separation process in the para-xylene separation unit 122 operates, preferably via simulated moving adsorption bed (SMB) employing a desorbent. Examples of desorbent include, and are not limited to para-diethylbenzene or toluene. Although not shown in the exemplary FIG. 1, the para-xylene separation unit may include a fractionation zone to obtain the para-xylene stream in line 124 and the raffinate stream in line 126. An exemplary fractionation zone may comprise an extract column and a raffinate column. In the instant exemplary aspect, a para-xylene extract stream may be withdrawn from the para-xylene separation unit and may be passed to the extract column which separates the para-xylene from the desorbent to provide the para-xylene stream comprising the desired para-xylene. Further, a first return desorbent stream may be withdrawn which may be subsequently recycled to the para-xylene separation unit 122. The para-xylene stream in line 124 may be passed to the finishing column (not shown) to separate a para-xylene product from the lighter hydrocarbons. Further, an intermediate raffinate stream comprising non-equilibrium mixture of $C_8$ aromatics raffinate and the desorbent may be also withdrawn from the para-xylene separation unit and may be passed to the raffinate column. The raffinate column separates the raffinate stream for isomerization in the first isomerization unit 128 from a second return desorbent stream. In accordance with another exemplary embodiment, para-xylene may be separated by fractional crystallization. In another aspect, para-xylene may be separated by combination of fractional crystallization and adsorptive separation.

Referring back to FIG. 1, the raffinate stream in line 126 comprising a non-equilibrium mixture of xylene isomers and ethylbenzene may be passed to a first isomerization unit to provide a first isomerization effluent in line 130. The raffinate stream is isomerized in the first isomerization unit 130, which contains an isomerization catalyst to provide a product approaching equilibrium concentrations of $C_8$ aromatic isomers. In accordance with the instant embodiment as discussed for producing para-xylene, additional para-xylene may be produced by reestablishing an equilibrium or near-equilibrium distribution of xylene isomers. In accordance with an exemplary embodiment as discussed, the isomerization catalyst is an ethylbenzene (EB) isomerization catalyst. In the first isomerization unit 128, the non-equilibrium mixture, depleted in para-xylene, is contacted with the ethylbenzene (EB) isomerization catalyst well-known in the art. The first isomerization effluent is withdrawn in line 130 from the first isomerization unit 128. The first isomerization effluent from the first isomerization unit 128 may be passed to the deheptanizer column 138.

Referring back to the ortho-xylene column 116, an ortho-xylene rich stream in 118 and an ortho-xylene column bottoms stream in line 120 comprising $C_{9+}$ alkylaromatic hydrocarbons may be withdrawn from the ortho-xylene column 116. In accordance with an exemplary embodiment, an amount of ortho-xylene in the $C_8$ aromatics stream and the ortho-xylene rich stream during the separation step may be controlled via a control system. Each control system includes any suitable structure for interacting with one or more sensors and controlling one or more actuators. Each controller could, for example, represent a multivariable controller, such as a [Robust Multivariable Predictive Control Technology (RMPCT)] controller or other type of controller implementing [model predictive control (MPC)] or other [advanced predictive control (APC)]. As a particular example, each controller could represent a computing device running a real-time operating system.

In an aspect, the control system may include one or more sensors, wherein the one or more sensors calculate the amount of ortho-xylene in the $C_8$ aromatics stream. Further, one or more process conditions may be changed in response to the step of calculation to limit the amount of ortho-xylene in the $C_8$ aromatics stream in case the amount of ortho-xylene is above a predetermined amount. In an aspect, the one or more process conditions may be changed via a feedback module present in the control system.

Subsequently, at least a portion of the ortho-xylene rich stream in line 118 may be passed to the second isomerization unit 132. In the second isomerization unit, the ortho-xylene stream may be contacted with an isomerization catalyst in liquid phase at isomerization conditions in substantial absence of hydrogen to produce a second isomerization effluent. In an aspect, isomerization in the second isomerization unit 132 takes place in complete absence of hydrogen.

In accordance with an exemplary embodiment as shown in FIG. 1, a first portion of the second isomerization effluent in line 134 may be passed to the deheptanizer column 138. In accordance with an exemplary embodiment, the first isomerization effluent may comprise at least about 60 wt %, preferably about 80 wt % and more preferably about 99 wt % of the isomerization effluent. In an aspect, the first isomerization effluent may comprise about 100 wt % of the isomerization effluent. Further, a second portion of isomerization effluent in line 136 may be passed to the para-xylene separation for further processing as described above. In accordance with an exemplary embodiment, the second portion of the isomerization effluent may comprise about 0 to about 40 wt. % of the isomerization effluent.

In the deheptanizer column 138, a deheptanizer bottoms stream in line 142 comprising $C_8$ aromatics including para-xylene is withdrawn. Typically, in processes using an EB Isomerization type catalyst, the deheptanizer bottoms stream is passed through an olefin treatment unit to treat residual olefin contaminants before being passed to the xylene column 110. Examples of the olefin treatment unit include, but are not limited to, a clay treater and an olefin reduction process (ORP) unit. In accordance with an exemplary embodiment as shown in FIG. 1, the deheptanizer bottoms stream in line 142 may be passed directly to the xylene column 110 without an intermediate step for removal of olefins. Accordingly, the xylene column 110 may be in direct, downstream communication with the deheptanizer column 138. In accordance with an exemplary embodiment as shown, a portion of the first isomerization effluent in line 135 may be mixed with the deheptanizer bottoms stream in line 142 and passed to the xylene column 110 Accordingly, in the instant aspect, a portion of the first isomerization effluent may bypass the deheptanizer column 138. In accordance with an exemplary embodiment, the portion of the first isomerization effluent may vary from about 0 to about 30 wt % of the isomerization effluent. A deheptanizer overhead stream in line 140 may also be withdrawn from the deheptanizer column 138 and may be passed to the stabilizer 172.

Referring back to the reformate splitter column 104, the reformate overhead stream in line 106 comprising $C_{7-}$ aromatic hydrocarbons may be passed to the aromatics extraction unit 144. Further, a stabilizer bottoms stream in line 176 may also be passed to the aromatics extraction unit 144. The aromatics extraction unit 144 can comprise different methods of separating aromatics from a hydrocarbon stream. One industry standard is the Sulfolane™ process, which is an extractive distillation process utilizing sulfolane solvent to facilitate high purity extraction of aromatics. The Sulfolane™ process is well known to those skilled in the art. An aromatics extract stream in line 148 comprising benzene and toluene and a raffinate stream in line 146 comprising non-aromatic hydrocarbons may be withdrawn from the aromatics extraction unit 144. The aromatics extract stream in line 148 may be passed to the BT column 154 to provide benzene and toluene via separation. In accordance with an exemplary embodiment as shown in FIG. 1, the aromatics extract stream in line 148 may be passed through a clay treater 150 to treat residual olefin contaminants and provide a treated aromatics extract stream in line 152 prior to being passed to the BT column 154. A transalkylation bottom stream in line 170 from the transalkylation stripper column 166 may also be passed to the BT column 154. A benzene-enriched stream in line 156 and a toluene-enriched stream in line 158 are withdrawn from the BT column 154. Further, the BT column bottoms stream in line 160 is withdrawn and sent to the xylene column 110 for further processing as described above. The toluene-enriched stream in line 158 may be passed to the transalkylation unit 162 for production of additional xylenes and benzene.

In accordance with an exemplary embodiment as shown in FIG. 1, in addition to a toluene-enriched stream, a heavy aromatics column overhead stream in line 180 rich in $C_9$ and $C_{10}$ alkylaromatics from the heavy aromatics column 178 may be passed to the transalkylation unit 162. A make-up hydrogen gas stream (not shown) may also be provided to the transalkylation unit 162. In the transalkylation unit 162, the incoming feedstreams may be contacted with a transalkylation catalyst under transalkylation conditions. In the transalkylation unit 162, the process continues by transalkylating $C_9$ and $C_{10}$ alkylaromatics with toluene. A transalkylated stream in line 164 comprising benzene and xylenes may be withdrawn from the transalkylation unit 162.

Transalkylation catalysts that can be used in the present disclosure include conventional transkylation catalysts such as those disclosed in U.S. Pat. No. 6,740,788, the teachings of which are incorporated herein by reference. Conditions employed in the transalkylation unit 162 normally include a temperature of from about 200° C. to about 540° C. The transalkylation unit 162 is operated at moderately elevated pressures broadly ranging from about 1 kg/cm$^2$ to about 60 kg/cm$^2$. The transalkylation reaction can be effected over a wide range of space velocities, with higher space velocities affecting a higher ratio of para-xylene at the expense of conversion. Liquid hourly space velocity generally is in the range of from about 0.1 to about 20 hr$^{-1}$.

The transalkylated stream in line 164 may be sent to the transalkylation stripper 166 to recover the transalkylation stripper bottoms stream in line 170. A net overhead stream in line 168 comprising $C_6$ and lighter hydrocarbons may also be withdrawn from the transalkylation stripper 166. Subsequently, the transalkylation stripper bottoms stream in line 170 may be recycled to the BT column 154 to recover benzene product and unconverted toluene for further processing as previously described. The net overhead stream in line 168 may be passed to the stabilizer 172 to provide a stabilizer overhead vaporous stream in line 174 and the stabilizer bottoms stream in line 176. The stabilizer bottoms stream in line 176 may be passed to the aromatics extraction unit 144.

Referring back to the ortho-xylene column 116, the ortho-xylene bottoms stream in line 120 rich in $C_9$ and heavier alkylaromatic hydrocarbons may be passed to the heavy aromatics column 178 to separate heavy aromatics comprising $C_{11+}$ alkylaromatic hydrocarbons from $C_9$ and $C_{10}$ alkylaromatics recovered as the heavy aromatics column overhead stream in line 178. The $C_{11+}$ alkylaromatic hydrocarbons may be withdrawn from the heavy aromatics column 178 as a bottoms stream in line 182. The heavy aromatics column overhead stream in line 178 rich in $C_9$ and $C_{10}$ alkylaromatics may be passed to the transalkylation unit 162 for production of additional xylenes and benzene as previously described.

In the instant flow scheme as described above, the first isomerization unit 128 i.e. the EB isomerization unit runs more efficiently with ortho-xylene lean feed resulting in lower ring loss. Further, the newly added second isomerization unit 132 i.e. liquid phase isomerization unit receives an ortho-xylene rich stream which can effectively isomerize the xylenes with a zeolite based catalyst. Since liquid phase isomerization unit is operated under liquid phase, and does not need hydrogen, there is saving in operating expenditures. The major benefit comes from the lowering of ring losses across the EB isomerization unit along with a para-xylene yield improvement of 1 to 2 wt % from the instant flow scheme.

Figure 2:
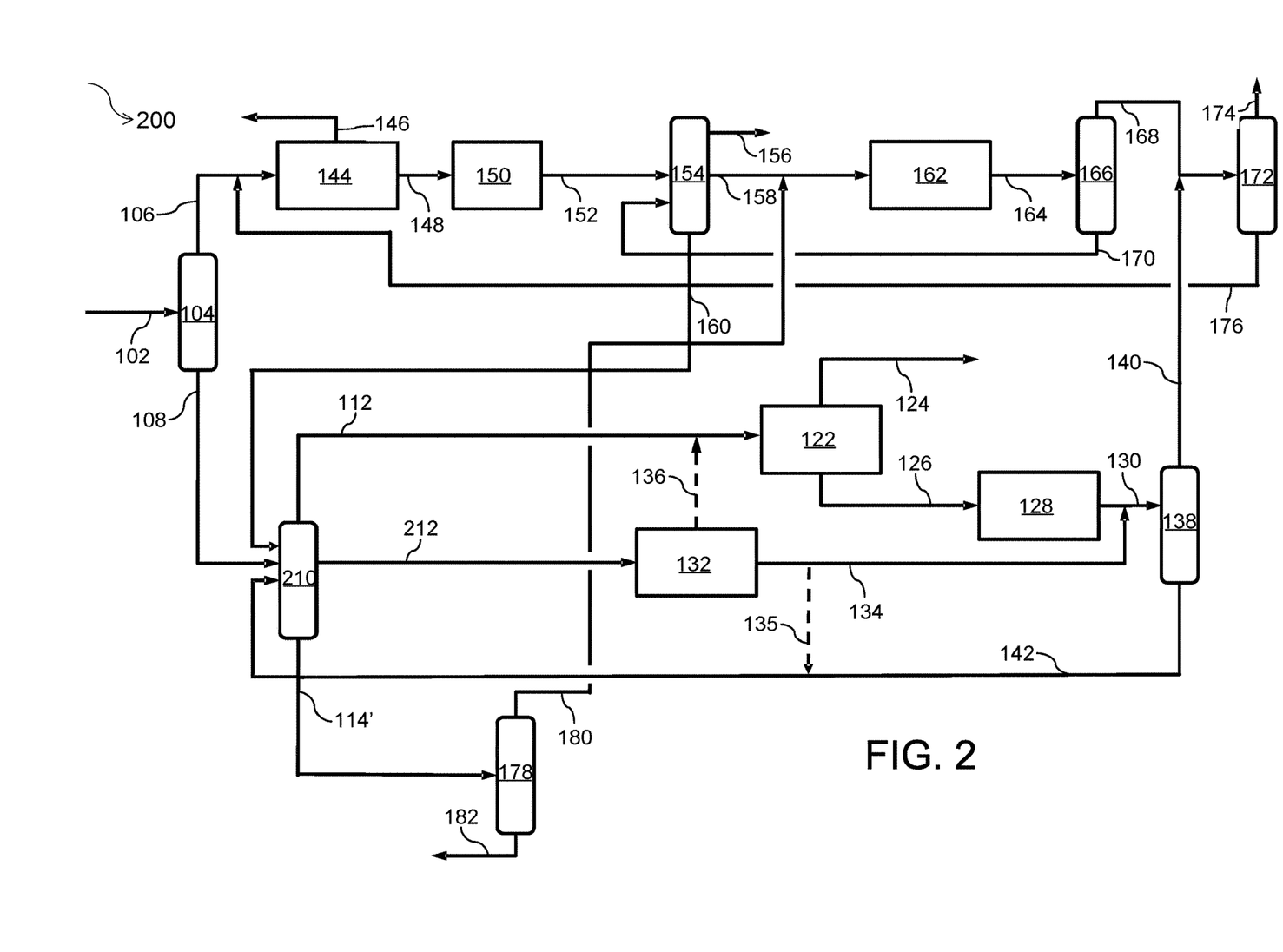
FIG. 2 illustrates an aromatics complex according to another embodiment of the present disclosure.

Turning now to FIG. 2, another embodiment of the aromatics complex is addressed with reference to a process and apparatus 200 for producing a para-xylene product in an aromatic complex. Many of the elements in FIG. 2 have the same configuration as in FIG. 1 and bear the same respective reference number and have similar operating conditions. Further, streams that have same configuration as in FIG. 1 but vary in composition bear the same reference numeral as in FIG. 1 but are marked with a prime symbol ('). The apparatus and process in FIG. 2 are the same as in FIG. 1 with the exception of the noted following differences. The apparatus 200 includes a xylene column 210 which provides the ortho-xylene rich stream. In accordance with an exemplary embodiment, the xylene column may be a divided wall column with the incoming feed streams being fed to one side of the column and the various product fractions being taken out from the other side of the xylene column 110. In accordance with an exemplary embodiment as shown in FIG. 2, an ortho-xylene rich stream in line 212 may be taken as a side draw in addition to the $C_8$ aromatics stream in line 112 and a xylene column bottoms stream comprising $C_{9+}$ alkylaromatic hydrocarbons in line 114'. Accordingly, the ortho-xylene rich stream is obtained from the xylene column without the need of a dedicated ortho-xylene column as per the instant embodiment.

The ortho-xylene rich stream in line 212 may be passed to the second isomerization unit 132 which will perform the same functions as described above with respect to the FIG. 1. Further, the xylene bottoms stream in line 114' may be passed to the heavy aromatics column 178 which will perform the same functions as described above with respect to the FIG. 1. The rest of the process flow is similar to what is described in FIG. 1.

In some embodiments, various functions described herein are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

SPECIFIC EMBODIMENTS

While the following is described in conjunction with specific embodiments, it will be understood that this description is intended to illustrate and not limit the scope of the preceding description and the appended claims.

A first embodiment of the invention is a process for the production of para-xylene, wherein the process comprises providing a hydrocarbon stream comprising $C_{7+}$ hydrocarbons; separating the hydrocarbon stream to provide a $C_8$ aromatics stream and an ortho-xylene rich stream; passing the $C_8$ aromatics stream to a para-xylene separation unit for separating para-xylene to provide a para-xylene stream and a raffinate stream; passing at least a portion of the raffinate stream to a first isomerization unit to provide a first isomerization effluent, wherein the first isomerization effluent is produced in the presence of an ethylbenzene (EB) isomerization catalyst; and contacting at least a portion of the ortho-xylene rich stream with an isomerization catalyst in a second isomerization unit in liquid phase at isomerization conditions in substantial absence of hydrogen to produce a second isomerization effluent. An embodiment of the invention is one, any or all of prior embodiments in this paragraph up through the first embodiment in this paragraph, wherein separating the hydrocarbon stream comprises passing the hydrocarbon stream to a xylene column to provide the $C_8$ aromatics stream from an overhead and a xylene bottoms stream comprising ortho-xylene and $C_{9+}$ alkylaromatic hydrocarbons; and passing the xylene bottoms stream to an ortho-xylene column to provide the ortho-xylene rich stream and an ortho-xylene column bottoms stream comprising $C_{9+}$ alkylaromatic hydrocarbons. An embodiment of the invention is one, any or all of prior embodiments in this paragraph up through the first embodiment in this paragraph, wherein separating the hydrocarbon stream comprises passing the hydrocarbon stream to the xylene column to provide the $C_8$ aromatics stream from an overhead and the ortho-xylene rich stream as a side draw from the xylene column. An embodiment of the invention is one, any or all of prior embodiments in this paragraph up through the first embodiment in this paragraph, wherein the xylene column is a divided wall column. An embodiment of the invention is one, any or all of prior embodiments in this paragraph up through the first embodiment in this paragraph further comprising passing the first isomerization effluent and a first portion of the second isomerization effluent to a deheptanizer column. An embodiment of the invention is one, any or all of prior embodiments in this paragraph up through the first embodiment in this paragraph, wherein a second portion of the second isomerization effluent is passed to the para-xylene separation unit. An embodiment of the invention is one, any or all of prior embodiments in this paragraph up through the first embodiment in this paragraph, wherein contacting the at least portion of the ortho-xylene rich stream in the second isomerization unit occurs in complete absence of hydrogen. An embodiment of the invention is one, any or all of prior embodiments in this paragraph up through the first embodiment in this paragraph, wherein separation in the para-xylene separation unit takes place by crystallization or adsorption. An embodiment of the invention is one, any or all of prior embodiments in this paragraph up through the first embodiment in this paragraph further comprising controlling an amount of ortho-xylene in the $C_8$ aromatics stream and the ortho-xylene rich stream during the separation step via a control system. An embodiment of the invention is one, any or all of prior embodiments in this paragraph up through the first embodiment in this paragraph further comprising calculating an amount of ortho-xylene in the $C_8$ aromatics stream and changing one or more process conditions in response to the step of calculation to limit the amount of ortho-xylene in the $C_8$ aromatics stream via a feedback module.

A second embodiment of the invention is a process for the production of para-xylene, wherein the process comprises providing a reformate stream comprising aromatic hydrocarbons to a reformate splitter to provide a reformate bottoms stream comprising $C_{7+}$ aromatic hydrocarbons and a reformate overhead stream comprising $C_{7-}$ aromatic hydrocarbons; passing the reformate bottoms stream to a xylene column to provide an $C_8$ aromatics stream and a xylene bottoms stream comprising ortho-xylene and $C_{9+}$ alkylaromatic hydrocarbons; passing the $C_8$ aromatics stream to a para-xylene separation unit for separating para-xylene, wherein the $C_8$ aromatics stream is contacted with an adsorbent under adsorption conditions to provide a para-xylene stream and a raffinate stream; passing the xylene bottoms stream to an ortho-xylene column to provide the ortho-xylene rich stream and an ortho-xylene column bottoms stream comprising $C_{9+}$ alkylaromatic hydrocarbons; passing at least a portion of the raffinate product stream to a first isomerization unit to provide a first isomerization effluent, wherein the first isomerization effluent is produced in the presence of an ethylbenzene (EB) isomerization catalyst; and contacting at least a portion of the ortho-xylene rich stream with an isomerization catalyst in a second isomerization unit in liquid phase at isomerization conditions in substantial absence of hydrogen to produce a second isomerization effluent. An embodiment of the invention is one, any or all of prior embodiments in this paragraph up through the second embodiment in this paragraph further comprising passing the first isomerization effluent and a first portion of the second isomerization effluent to a deheptanizer column. An embodiment of the invention is one, any or all of prior embodiments in this paragraph up through the second embodiment in this paragraph, wherein a second portion of the second isomerization effluent is passed to the para-xylene separation unit. An embodiment of the invention is one, any or all of prior embodiments in this paragraph up through the second embodiment in this paragraph, wherein contacting the at least portion of the ortho-xylene rich stream in the second isomerization occurs in complete absence of hydrogen. An embodiment of the invention is one, any or all of prior embodiments in this paragraph up through the second embodiment in this paragraph further comprising calculating an amount of ortho-xylene in the $C_8$ aromatics stream and changing one or more process conditions in response to the step of calculation to limit the amount of ortho-xylene in the $C_8$ aromatic stream via a feedback module.

A third embodiment of the invention is a process for the production of para-xylene, wherein the process comprises providing a reformate stream comprising aromatic hydrocarbons to a reformate splitter to provide a reformate bottoms stream comprising $C_{7+}$ aromatic hydrocarbons and a reformate overhead stream comprising $C_{7-}$ aromatic hydrocarbons; passing the reformate bottoms stream to a xylene column to provide a $C_8$ aromatics stream from an overhead, an ortho-xylene rich stream as a side draw and a xylene column bottoms stream comprising $C_{9+}$ alkylaromatic hydrocarbons; passing the $C_8$ aromatics stream to a para-xylene separation unit for separating para-xylene to provide a para-xylene stream and a raffinate stream; passing at least a portion of the raffinate stream to a first isomerization unit to provide a first isomerization effluent, wherein the first isomerization effluent is produced in the presence of an ethylbenzene (EB) isomerization catalyst; and contacting at least a portion of the ortho-xylene rich stream with an isomerization catalyst in a second isomerization unit in liquid phase at isomerization conditions in substantial absence of hydrogen to produce a second isomerization effluent. An embodiment of the invention is one, any or all of prior embodiments in this paragraph up through the third embodiment in this paragraph further comprising passing the first isomerization effluent and a first portion of the second isomerization effluent to a deheptanizer column. An embodiment of the invention is one, any or all of prior embodiments in this paragraph up through the third embodiment in this paragraph, wherein contacting of the at least portion of the ortho-xylene rich stream in the second isomerization occurs in complete absence of hydrogen. An embodiment of the invention is one, any or all of prior embodiments in this paragraph up through the third embodiment in this paragraph, wherein the xylene column is a divided wall column. An embodiment of the invention is one, any or all of prior embodiments in this paragraph up through the third embodiment in this paragraph further comprising calculating an amount of ortho-xylene in the $C_8$ aromatics stream and changing one or more process conditions in response to the step of calculation to limit the amount of ortho-xylene in the $C_8$ aromatics stream via a feedback module.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for the production of para-xylene, wherein the process comprises:
   providing a hydrocarbon stream comprising $C_{7+}$ hydrocarbons;
   separating the hydrocarbon stream in a xylene column to provide a $C_8$ aromatics stream comprising para-xylene, meta-xylene, and ethylbenzene, and an ortho-xylene rich stream containing at least 70 mol % ortho-xylene;
   passing the $C_8$ aromatics stream to a para-xylene separation unit for separating para-xylene to provide a para-xylene stream and a single raffinate stream comprising ethylbenzene and a non-equilibrium mixture of xylene isomers depleted of para-xylene;
   passing at least a portion of the single raffinate stream from the para-xylene separation unit to a first isomerization unit to provide a first isomerization effluent comprising an equilibrium or near equilibrium mixture of xylene isomers, wherein the first isomerization effluent is produced in the presence of an ethylbenzene (EB) isomerization catalyst; and
   contacting at least a portion of the ortho-xylene rich stream from the xylene column with an isomerization catalyst in a second isomerization unit in liquid phase at isomerization conditions in substantial absence of hydrogen to produce a second isomerization effluent, wherein a total feed to the second isomerization unit contains at least 70 mol % ortho-xylene.

2. The process of claim 1, wherein separating the hydrocarbon stream comprises:
   passing the hydrocarbon stream to a xylene column to provide the $C_8$ aromatics stream from an overhead and a xylene bottoms stream comprising orthoxylenes and $C_{9+}$ alkylaromatic hydrocarbons; and
   passing the xylene bottoms stream to an ortho-xylene column to provide the orthoxylene rich stream and an ortho-xylene column bottoms stream comprising $C_{9+}$ alkylaromatic hydrocarbons.

3. The process of claim 1, wherein separating the hydrocarbon stream comprises passing the hydrocarbon stream to the xylene column to provide the $C_8$ aromatics stream from an overhead and the ortho-xylene rich stream as a side draw from the xylene column.

4. The process of claim 3, wherein the xylene column is a divided wall column.

5. The process of claim 1, wherein a second portion of the second isomerization effluent is passed to the para-xylene separation unit.

6. The process of claim 1, wherein the contacting the at least a portion of the ortho-xylene rich stream in the second isomerization unit occurs in complete absence of hydrogen.

7. The process of claim 1, wherein the separating in the para-xylene separation unit takes place by crystallization or adsorption.

8. The process of claim 1 further comprising controlling an amount of ortho-xylene in the $C_8$ aromatics stream and the ortho-xylene rich stream during the separating step via a control system.

9. The process of claim 1 further comprising a step of calculating an amount of ortho-xylene in the $C_8$ aromatics stream and changing one or more process conditions in response to the step of calculating to limit the amount of ortho-xylene in the $C_8$ aromatics stream via a feedback module.

10. A process for the production of para-xylene, wherein the process comprises:
    providing a reformate stream comprising aromatic hydrocarbons to a reformate splitter to provide a reformate bottoms stream comprising $C_{7+}$ aromatic hydrocarbons and a reformate overhead stream comprising $C_{7-}$ aromatic hydrocarbons;
    passing the reformate bottoms stream to a xylene column to provide an $C_8$ aromatics stream comprising para-xylene, meta-xylene, and ethylbenzene, and a xylene bottoms stream comprising ortho-xylenes and $C_{9+}$ alkylaromatic hydrocarbons;
    passing the $C_8$ aromatics stream to a para-xylene separation unit for separating para-xylene, wherein the $C_8$ aromatics stream is contacted with an adsorbent under adsorption conditions to provide a para-xylene stream and a single raffinate stream comprising ethylbenzene and a non-equilibrium mixture of xylene isomers depleted of para-xylene;
    passing the xylene bottoms stream to an ortho-xylene column to provide an ortho-xylene rich stream containing at least 70 mol % ortho-xylene and an ortho-xylene column bottoms stream comprising $C_{9+}$ alkylaromatic hydrocarbons;
    passing at least a portion of the single raffinate stream from the para-xylene separation unit to a first isomerization unit to provide a first isomerization effluent comprising an equilibrium or near equilibrium mixture of xylene isomers, wherein the first isomerization effluent is produced in the presence of an ethyl benzene (EB) isomerization catalyst; and contacting at least a portion of the ortho-xylene rich stream from the ortho-xylene column with an isomerization catalyst in a second isomerization unit in liquid phase at isomerization conditions in substantial absence of hydrogen to produce a second isomerization effluent, wherein a total feed to the second isomerization unit contains at least 70 mol % ortho-xylene.

11. The process of claim 10, wherein a second portion of the second isomerization effluent is passed to the para-xylene separation unit.

12. The process of claim 10, wherein the contacting the at least a portion of the ortho-xylene rich stream in the second isomerization unit occurs in complete absence of hydrogen.

13. The process of claim 10 further comprising a step of calculating an amount of ortho-xylene in the $C_8$ aromatics stream and changing one or more process conditions in response to the step of calculating to limit the amount of ortho-xylene in the $C_8$ aromatic stream via a feedback module.

14. A process for the production of para-xylene, wherein the process comprises:

providing a reformate stream comprising aromatic hydrocarbons to a reformate splitter to provide a reformate bottoms stream comprising $C_{7+}$ aromatic hydrocarbons and a reformate overhead stream comprising $C_{7-}$ aromatic hydrocarbons;

passing the reformate bottoms stream to a xylene column to provide a $C_8$ aromatics stream comprising para-xylene, meta-xylene, and ethylbenzene from an overhead, an ortho-xylene rich stream containing at least 70 mol % ortho-xylene as a side draw, and a xylene column bottoms stream comprising $C_{9+}$ alkylaromatic hydrocarbons;

passing the $C_8$ aromatics stream to a para-xylene separation unit for separating para-xylene to provide a para-xylene stream and a single raffinate stream comprising ethylbenzene and a non-equilibrium mixture of xylene isomers depleted of para-xylene;

passing at least a portion of the single raffinate stream from the para-xylene separation unit to a first isomerization unit to provide a first isomerization effluent comprising an equilibrium or near equilibrium mixture of xylene isomers, wherein the first isomerization effluent is produced in the presence of an ethylbenzene (EB) isomerization catalyst; and contacting at least a portion of the ortho-xylene rich stream from the xylene column with an isomerization catalyst in a second isomerization unit in liquid phase at isomerization conditions in substantial absence of hydrogen to produce a second isomerization effluent, wherein a total feed to the second isomerization unit contains at least 70 mol % ortho-xylene.

15. The process of claim 14, wherein the contacting of the at least a portion of the ortho-xylene rich stream in the second isomerization occurs in complete absence of hydrogen.

16. The process of claim 14, wherein the xylene column is a divided wall column.

17. The process of claim 14, further comprising a step of calculating an amount of ortho-xylene in the $C_8$ aromatics stream and changing one or more process conditions in response to the step of calculating to limit the amount of ortho-xylene in the $C_8$ aromatics stream via a feedback module.

18. The process of claim 1 further comprising passing the first isomerization effluent and a first portion of the second isomerization effluent to a deheptanizer column.

19. The process of claim 10 further comprising passing the first isomerization effluent and a first portion of the second isomerization effluent to a deheptanizer column.

20. The process of claim 1 wherein the ortho-xylene rich stream contains at least 90 mol % ortho-xylene, and wherein the total feed to the second isomerization unit contains at least 90 mol % ortho-xylene.

* * * * *